United States Patent [19]

Cremer et al.

[11] Patent Number: 5,175,379
[45] Date of Patent: Dec. 29, 1992

[54] PROCESS FOR THE PREPARATION OF PARTLY FLOURINATED ETHANES

[75] Inventors: Hans R. Cremer, Kerpen; Harald Noichl, Kelkheim, both of Fed. Rep. of Germany

[73] Assignee: Hoechst AG, Frankfurt am Main, Fed. Rep. of Germany

[21] Appl. No.: 644,414

[22] Filed: Jan. 22, 1991

Related U.S. Application Data

[63] Continuation of Ser. No. 398,063, Aug. 24, 1989, abandoned.

[30] Foreign Application Priority Data

Aug. 27, 1988 [DE] Fed. Rep. of Germany ....... 3829098

[51] Int. Cl.$^5$ .............................................. C07C 19/08
[52] U.S. Cl. ................................................. 570/163
[58] Field of Search ........................................ 570/163

[56] References Cited

U.S. PATENT DOCUMENTS 2,748,177  5/1956  Miller et al.
4,145,368  3/1979  Sweeney et al. ................. 570/183
4,547,483  10/1985  Müller et al.

Primary Examiner—N. Alan Siegel

[57] ABSTRACT

A process for the preparation of partly fluorinated ethanes of the general formula $$CF_3—CFH_xCl_{2-x}$$

in which x=0, 1 or 2, is indicated which comprises reacting, as the reactant, partly fluorinated ethane of the general formula $$C_2F_3H_xCl_{3-x}$$

in which x=0, 1, or 2, and, as the fluorinating agent, partly fluorinated ethanes of the general formula $$CF_{3-x}Cl_x—CH_{3-y}Cl_y$$

in which x=0, 1 or 2 and y=0, 1, 2 or 3 with one another in gaseous form in the presence of a chromium catalyst at temperatures of 150° to 600° C., the reactant and the fluorinating agent having the same chemical structural formula being excluded.

1 Claim, No Drawings

PROCESS FOR THE PREPARATION OF PARTLY FLOURINATED ETHANES

This is a continuation of our co-pending application Ser. No. 07/398,063, filed Aug. 24, 1918, now abandoned.

The invention relates to a process for the preparation of partly fluorinated ethanes of the general formula $$CF_3-CFH_xCl_{2-x}$$

in which x = 0, 1 or 2.

Partly fluorinated ethanes of the general formula $CF_3-CFH_xCl_{2-x}$ have desirable properties (chemically inert, difficult to ignite, non-toxic and not aggressive towards material) of the perhalogenated fluorochlorohydrocarbons. The perhalogenated fluorochlorohydrocarbons are held responsible for the breakdown of the upper ozone layer which protects the earth's surface from intensive UV radiation. Partly fluorinated ethanes of the general formula $CF_3-CFH_xCl_{2-x}$ (x=0, 1 or 2) are either chlorine-free or already for the most part degraded in the lower layers of the atmosphere and are therefore only a low potential hazard for the upper ozone layer.

There is therefore a considerable interest in partly fluorinated ethanes as a substitute, which does not destroy the upper ozone layer, instead of perhalogenated fluorochlorohydrocarbons.

Partly fluorinated ethanes are prepared in accordance with U.S. Pat. No. 2,748,177 by reaction of $CCl_4$, $CCl_3-CClF_2$, $CClF_2-CF_3$ or $CCl_2FCClF_2$ with anhydrous hydrogen fluoride on an aluminum fluoride catalyst at temperatures of 175 to 450° C. The disadvantage of this process is, in addition to the difficult handling of hydrogen fluoride, the formation of structural isomer mixtures of partly fluorinated ethanes, which in some cases can be separated only under expensive distillation conditions. In addition, a considerable amount of fluorochloroethanes which cannot be utilized economically are obtained in this procedure.

There was the object of providing a process for the preparation of partly fluorinated ethanes of the general formula $$CF_3CFH_xCl_{2-x}$$

in which x=0, 1 or 2, which allows controlled preparation, with a high selectivity, of these compounds, which can be isolated as the pure product without great expenditure on distillation.

The invention relates to a process for the preparation of partly fluorinated ethanes of the general formula $$CF_3CFH_xCl_{2-x}$$

in which x=0, 1 or 2, which comprises reacting, as the reactant, partly fluorinated ethane of the general formula $$C_2F_3H_xCl_{3-x}$$

in which x=0, 1 or 2 and, as the fluorinating agent, partly fluorinated ethanes of the general formula $$CF_{3-x}Cl_x-CH_{3-y}Cl_y,$$

in which x=0, 1 or 2 and y =0, 1, 2 or 3 with one another in gaseous form in the presence of a chromium catalyst at temperatures of 150° to 600° C., the reactant and the fluorinating agent having the same chemical structural formula being excluded. In reactions in which the reactant and fluorinating agent are identical, when this compound is passed in gaseous form over the chromium catalyst a dismutation reaction occurs, in which only very low conversion into a large number of compounds takes place, as is described in the following Comparison Example 1.

It has been found that the desired partly fluorinated ethanes are obtained in a particularly high selectivity if partly fluorinated ethane of the general formula $$CF_3-CH_xCl_{3-x}$$

in which x=0, 1 or 2, is employed as the reactant, which is therefore preferred.

Chromium(III) compounds, such as oxides, hydroxides, nitrates or halides, are used as the chromium catalyst for the process according to the invention. The chromium(III) compounds are preferably activated before being employed for transfluorination with gaseous hydrogen fluoride.

Particularly high selectivities are achieved if the chromium catalyst is employed together with a support, such as magnesium oxide or graphite, and the supported chromium catalyst is activated by a hydrogen fluoride treatment. One possibility for the preparation of the supported chromium catalyst is described in U.S. Pat. No. 4,547,483.

This supported chromium catalyst consists of at least 55 % by weight of magnesium fluoride and 0.5 to 29 % by weight of chromium and has an atomic ratio of magnesium:chromium = 1.5 to 50. Chromium is present in this catalyst as chromium oxyfluoride.

To prepare the supported chromium catalyst just mentioned, 1 mol of a water-soluble chromium(III) salt is reacted with at least 1.5 mol of magnesium hydroxide or magnesium oxide in the presence of water, and the reaction mixture is thus converted, if appropriate by evaporation, into a paste containing chromium hydroxide and a magnesium salt. The paste is dried and treated with hydrogen fluoride at temperatures of 20 to 500° C. The paste can furthermore also contain MgO or Mg(OH)$_2$, depending on the excess of magnesium used.

The treatment with hydrogen fluoride is advantageously carried out at a temperature of 100 to 400° C. The catalyst is treated with at least 2 mol of hydrogen fluoride per mol of metal compound employed (chromium salt, magnesium oxide). The fluorination time is 0.5 to 10 hours. In order to effect more rapid removal of the water formed and to avoid undesirable temperature peaks, HF can be diluted by an inert gas (for example N$_2$ or air).

It is also possible to prepare catalysts of virtually identical empirical composition by mixing pulverulent hydrated chromium oxide with pulverulent magnesium fluoride and treating the mixture with hydrogen fluoride.

A high selectivity of the process according to the invention is achieved if it is carried out at a temperature of 250° to 400° C., in particular 320° to 360° C. The process according to the invention operates equally well under reduced, normal or elevated pressure.

To achieve high conversions, an average contact time of 1 to 300 seconds, in particular 10 to 100 seconds, should be maintained during the reaction. The average contact time is calculated from the formula:

$$\text{Average contact time } [S] = \frac{\text{Volume of the catalyst [ml]}}{\text{Volume of starting substances fed in per second [ml/s]}}$$

Particularly high selectivities are achieved if a molar ratio of reactant:fluorinating agent =(1 to 15):(10 to 1), preferably (1 to 7):(5 to 1), is established.

It has furthermore been found that an excess of reactant has a favorable influence on the selectivity of the reaction.

The process according to the invention also gives good results is a mixture of partly fluorinated ethanes of the general formula $$CF_{3-x}Cl_x-CH_{3-y}Cl_y$$

in which x=0, 1 or 2 and y=0, 1, 2 or 3, is employed as the fluorinating agent.

Equations of possible reactions according to the invention are listed in Table 1:

fluoride in a subsequent fluorination stage and employed again as fluorinating agent.

A suitable embodiment of the process according to the invention is the following: the reactant and the fluorinating agent are first vaporized and mixed in gaseous form in a mixing zone and heated to the reaction temperature. This gas mixture is fed into the contact zone. The contact zone consists of a temperature-controlled tube in which a loose pile of catalyst is located. The reaction products are condensed and the organic phase is subjected to fractional distillation.

The nomenclature of the fluorohydrocarbons is according to the method customary in the art, which is explained in "Römpps Chemie-Lexikon (Römpps Chemical Dictionary)", Frankh'sche Verlangshandlung, Stuttgart, (1973), volume 2, page 1172.

The invention is illustrated in more detail with the aid of the following examples.

The individual fractions were analyzed by gas chromatography and additionally identified with the $^{19}F$ and $^{1}H$-NMR method. The percentages stated are percentages by weight.

TABLE 1

| Reactant | Fluorinating agent | End product | By-product |
|---|---|---|---|
| 3 $CF_3-CCl_3$ + | $CF_3-CH_2Cl \rightarrow$ | 3 $CF_3-CFCl_2$ + | $CCl_2=CHCl + HCl$ |
| 2 $CF_3-CCl_3$ + | $CClF_2-CH_2Cl \rightarrow$ | 2 $CF_3-CFCl_2$ + | $CCl_2=CHCl + HCl$ |
| $CF_3-CCl_3$ + | $CCl_2F-CH_2Cl \rightarrow$ | $CF_3-CFCl_2$ + | $CCl_2=CHCl + HCl$ |
| 3 $CF_3-CCl_3$ + | $CF_3-CHCl_2 \rightarrow$ | 3 $CF_3-CFCl_2$ + | $CCl_2=CCl_2 + HCl$ |
| 2 $CF_3-CCl_3$ + | $CF_3-CHCl_2 \rightarrow$ | 2 $CF_3-CFCl_2$ + | $CCl_2=CClF + HCl$ |
| 2 $CF_3-CCl_3$ + | $CClF_2-CHCl_2 \rightarrow$ | 2 $CF_3-CFCl_2$ + | $CCl_2=CCl_2 + HCl$ |
| $CF_3-CCl_3$ + | $CClF_2-CHCl_2 \rightarrow$ | $CF_3-CFCl_2$ + | $CCl_2=CClF + HCl$ |
| $CF_3-CCl_3$ + | $CClF_2-CHCl_2 \rightarrow$ | $CF_3-CFCl_2$ + | $CCl_2=CCl_2 + HCl$ |
| 2 $CF_3-CCl_3$ + | $CF_3-CH_3 \rightarrow$ | 2 $CF_3-CFCl_2$ + | $CCl_2=CH_2 + HF$ |
| $CF_3-CCl_3$ + | $CClF_2-CH_3 \rightarrow$ | $CF_3-CFCl_2$ + | $CCl_2=CH_2 + HF$ |
| $CF_3-CCl_3$ + | $CCl_2F-CH_3 \rightarrow$ | $CF_2-CFCl_2$ | $CCl_2=CH_2 + HCl$ |
| $CF_3-CCl_3$ + | $CClF_2-CCl_3 \rightarrow$ | $CF_3-CFCl_2$ + | $CCl_2=CCl_2 + Cl_2$ |
| 2 $CF_3-CHCl_2$ + | $CF_3-CH_2Cl \rightarrow$ | 2 $CF_3-CHFCl$ + | $CCl_2=CHCl + HF$ |
| $CF_3-CHCl_2$ + | $CClF_2-CH_2Cl \rightarrow$ | $CF_3-CHFCl$ + | $CCl_2=CHCl + HF$ |
| $CF_3-CH_2Cl$ + | $CClF_2-CH_2Cl \rightarrow$ | $CF_3-CH_2F$ + | $CCl_2=CHCl + HF$ |
| 2 $CF_3-CHCl_2$ + | $CF_3-CH_3 \rightarrow$ | 2 $CF_3-CHFCl$ + | $CCl_2=CH_2 + HF$ |
| $CF_3-CHCl_2$ + | $CClF_2-CH_3 \rightarrow$ | $CF_3-CHFCl$ + | $CCl_2=CH_2 + HF$ |
| 2 $CF_3-CH_2Cl$ + | $CF_3-CH_3 \rightarrow$ | 2 $CF_3-CH_2F$ + | $CCl_2=CH_2 + HF$ |
| $CF_3-CH_2Cl$ + | $CClF_2-CH_3 \rightarrow$ | $CF_3-CH_2F$ + | $CCl_2=CH_2 + HF$ |

Particularly high conversions are achieved with the following fluorinating agents listed in Table 2, individually or as a mixture with one another:

TABLE 2

| Fluorinating agent | Formula |
|---|---|
| 1,1-Dichloro-1-fluoroethane | $CCl_2F-CH_3$ |
| 1-Chloro-1,1-difluoroethane | $CClF_2-CH_3$ |
| 1,1,1-Trifluoroethane | $CF_3-CH_3$ |
| 1-Fluoro-1,1,2-trichloroethane | $CCl_2F-CH_2Cl$ |
| 1,2-Dichloro-1,1-difluoroethane | $CClF_2-CH_2Cl$ |
| 1-Chloro-2,2,2-trifluoroethane | $CF_3-CH_2Cl$ |
| 1-Fluoro-1,1,2,2-tetrachloroethane | $CCl_2F-CHCl_2$ |
| 1,1-Difluoro-1,2,2-trichloroethane | $CClF_2-CHCl_2$ |
| 1,1-Dichloro-2,2,2-trifluoroethane | $CF_3-CHCl_2$ |
| Fluoropentachloroethane | $CCl_2F-CCl_3$ |
| 1,1-Difluoro-tetrachloroethane | $CClF_2-CCl_3$ |

The advantage is that the desired partly fluorinated ethanes can easily be isolated in a pure form from the reaction product by fractional distillation because of their low boiling point.

If the fluorinating agent is employed in excess, the excess fluorinating agent can be used again as the fluorinating agent together with the by-products formed, or the by-products formed are regenerated with hydrogen

EXAMPLE 1

30 ml of chromium/magnesium catalyst prepared according to U.S. Pat. No. 4,547,483 were introduced into an electrically heated glass tube 50 cm in length and 1 cm in internal diameter. 1,1,1-Trichloro-trifluoroethane (R113a) and 1-chloro-2,2,2-trifluoroethane (R133a) were vaporized, mixed in a temperature-controlled tube 70 cm long and passed over the catalyst at a molar ratio of 3.5:1. The average catalyst contact time was 37 seconds. The experiment was carried out at various temperatures for in each case 12 hours. The results are shown in Table 3.

TABLE 3

| | Temperatures (°C.) | | | | |
|---|---|---|---|---|---|
| Components | 80 | 300 | 320 | 340 | 360 |
| $CF_3CFCl_2$ (end product) | 16.4% | 24.5% | 42.9% | 52.9% | 58.4% |
| $CF_3CCl_3$ (reactant) | 66.2% | 57.8% | 39.0% | 26.0% | 19.7% |
| $CF_3-CH_2Cl$ (fluorinating agent) | 11.8% | 10.3% | 5.1% | 3.3% | 1.1% |
| $CCl_2=CHCl$ (by-product) | 4.6% | 6.6% | 11.8% | 14.7% | 16.3% |
| other products | <1.0% | <1.0% | 1.2% | 3.1% | 4.5% |
| Conversion (based on R133a): | 24.3% | 35.6% | 66.1% | 78.8% | 92.6% |
| Conversion (based | 21.4% | 31.7% | 54.7% | 69.0% | 76.5% |

TABLE 3-continued

| Components | Temperatures (°C.) | | | | |
|---|---|---|---|---|---|
| | 80 | 300 | 320 | 340 | 360 |
| on R113a): | | | | | |

An increase in temperature at the catalyst leads to an increase in conversion; however, the content of other products also increases.

EXAMPLE 2

1,1,1-Trichloro-trifluoroethane (R113a) and 1-chloro-2,2,2-trifluoroethane (R133a) were passed in a molar ratio of 0.6:1 over the chromium/magnesium catalyst (as in Example 1) at 340° C in the experimental set-up of Example 1. The average catalyst residence time was 21 seconds. The experiment was carried out for 10 hours. The result was as follows:
$CF_3—CFCl_2$:14.2%
$CF_3—CCl_3$:32.3%
$CF_3—CH_2Cl$:45.6%
$CCl_2=CHCl$:4.0%
$CF_3—CHCl_2$:<0.2%
other products:3.7%
Conversion:32.7% (based on R113a)

The comparison of Examples 2 and 1 (340° C) shows that a higher content of reactant in the gas mixture leads to an increase in selectivity.

EXAMPLE 3

30 ml of chromium oxyfluoride catalyst which had first been prepared from hydrated chromium oxide (Guignet's green) with $HF/N_2$ by the method described in the Patent U.S. Pat. No. 4,145,368 were placed in the experimental set-up of Example 1. 1,1,1-Trichloro-trifluoroethane (R113a) and 1-chloro-2,2,2-trifluoroethane (R133a) were passed over the catalyst at 340° C. The molar ratios, the contact times and the amounts of organic components are summarized in Table 4. The experiment was carried out for 12 hours.

TABLE 4

| Molar ratio of R113a:R133A | 0.6:1 | 3.5:1 |
|---|---|---|
| Average contact time: (seconds) | 21 | 37 |
| Components: | | |
| $CF_3—CFCl_2$ (end product) | 8.9% | 32.3% |
| $CF_3—CCl_3$ (reactant) | 37.9% | 46.9% |
| $CF_3CH_2Cl$ (fluorinating agent) | 46.3% | 7.4% |
| $CCl_2=CHCl$ (by-product) | 2.6% | 9.2% |
| $CF_3—CHCl_2$ (by-product) | 1.3% | 1.2% |
| other products | 3.1% | 3.0% |
| Conversion based on R113a: | 21.7% | 43.1% |
| Conversion based on R133a: | | 52.7% |

Example 3 shows the use of a different catalyst to that in Examples 1 and 2.

EXAMPLE 4

1,1,1-trichloro-trifluoroethane (R113a) and 1,1-difluoro-1,2,2-trichloroethane (R122) were reacted in a molar ratio of 3.4 1 at a temperature of 340° C. in the experimental set-up of Example 1, filled with chromium/magnesium catalyst as in Example 1. The average catalyst contact time was 42 seconds. The experiment was carried out for 12 hours. The result was as follows:
$CF_3—CFCl_2$ (end product):45.8%
$CF_3—CCl_3$ (reactant):30.0%
$CF_2Cl—CHCl_2$ (fluorinating agent):0.8%
$CCl_2=CCl_2$ (by-product):12.1%
$CCl_2=CClF$ ('):8.3%
other products:3.8%

Conversion
based on R122:96.5%
based on R113a:62.6%

EXAMPLE 5

A mixture of 1,1,1-trichloro-trifluoroethane (R113a) and 1,2-dichloro-1,1-difluoroethane (R132b) in a molar ratio of 4.1:1 was passed over the catalyst described in Example 1 at a temperature of 340° C in the experimental set-up of Example 1. The average catalyst contact time was 42 seconds. The experiment was carried out for 12 hours. The result was as follows:
$CF_3—CFCl_2$ (end product):38.1%
$CF_3—CCl_3$ (reactant):44.6%
$CF_2Cl—CH_2Cl$ (fluorinating agent):<0.1%
$CCl_2=CHCl$ (by-product):14.3%
other products:2.9%

Conversion
based on R132b:>99.9%
based on R113a:48.4%

Examples 4 and 5 differ from the above Examples 1 to 3 by the choice of fluorinating agent.

EXAMPLE 6

Various mixtures of $CF_3—CHCl_2$ (R123) and $CF_3—CH_2Cl$ (R133a) were passed over the chromium/magnesium catalyst described in Example 1 at 360° C in the experimental set-up of Example 1.

The average catalyst contact times, molar ratios and amounts of organic components are summarized in Table 6. The experiment was carried out for 12 hours.

TABLE 6

| Molar ratio of R123:R133a: | 0.8:1 | 1.8:1 | 2.6:1 | 4.4:1 |
|---|---|---|---|---|
| Average contact time (seconds) | 18 | 19 | 23 | 22 |
| Components: | | | | |
| $CF_3—CFHCl$ (end product) | 18.0% | 15.4% | 21.2% | 19.1% |
| $CF_3CH_2Cl$ (fluorinating agent) | 37.6% | 22.7% | 9.9% | 5.6% |
| $CF_3CHCl_2$ (reacant) | 27.6% | 52.5% | 48.7% | 60.7% |
| $CCl_2=CHCl$ (by product) | 11.5% | 7.4% | 12.7% | 9.7% |
| other products | 6.6% | 5.9% | 7.1% | 4.9% |
| Conversion | | | | |
| based on R123: | 42.3% | 24.7% | 32.7% | 26.1% |
| based on R133a: | | | 48.2% | 59.3% |

EXAMPLE 7

30 ml of the chromium/magnesirua catalyst described in Example 1 were introduced into the reactor described in that example. 1,1-dichloro-2,2,2-trifluoroethane (R123) and 1,1,1-trifluoroethane (R143a) in a molar ratio of 2.6:1 were metered in at 360° C.

The catalyst contact time was 29 seconds. The experiment was carried out for 12 hours. Analysis by gas chromatography gave the following composition for the organic product content:
$CF_3—CHFCl$ (end product):15.0%
$CF_3—CH_3$ (fluorinating agent):13.3%
$CF_3—CHCl_2$ (reactant):65.5%
$CCl_2=CH_2$ (by-product):4.9%
other products:1.3%

Conversion based on R143a:25.8%
based on R123:20.4%

EXAMPLE 8

1-Chloro-2,2,2-trifluoroethane (R133a) and 1,1,1-trifluoroethane (R143a) were passed in a ratio of 2.2:1 over the chromium/magnesium catalyst at 400° C. in the experimental set-up from Example 1. The catalyst contact time was 29 seconds. The experiment was carried out for 12 hours. Analysis of the organic part of the crude product by gas chromatography gave the following composition:
$CF_3$—$CH_2F$ (end product):7.9%
$CF_3$—$CH_3$ (fluorinating agent):23.1%
$CF_3$—$CH_2Cl$ (reactant):60.5%
other products:8.5%
($CCl_2$=$CH_2$, $CF_2$=$CHCl$)

Conversion based on R143a:12.3%
based on R133a:11.1%

Examples 6 to 8 document the subject matter of the invention for other reactant/fluorinating agent reactions.

COMPARISON EXAMPLE 1 Example of the dismutation

Example 1 was repeated with the change that 1,1,1-tri-chloro-trifluoroethane was passed over the chromium/magnesium catalyst of Example 1 at 340° C without fluorinating agent. The average catalyst contact time was 37 seconds. The experiment was carried out for 12 hours. The result was as follows:
$CF_3$—$CFCl_2$ (end product):1.2%
$CF_3$—$CCl_3$ (reactant):97.5%
other products:1.1%

COMPARISON EXAMPLE 2

Example 1 was repeated, but aluminum fluoride was now investigated as the catalyst. The catalyst was prepared from activated aluminum oxide (Harshaw/Filtrol, Cleveland, Ohio) in accordance with U.S.-A-3,087,974 with $CCl_2F$—$CClF_2$ (R113). Various mixtures of $CF_3$—$CCl_3$ (R113a) and $CF_3$—$CH_2Cl$ (R133a) were then passed over the catalyst at 340° C. The average contact times, molar ratios and amounts of the organic components are noted in Table 5. The experiment was carried out for 12 hours.

TABLE 5

| Molar ratio of R113a:R133a: | 0.5:1 | 3.7:1 |
|---|---|---|
| Average contact time: (seconds) | 21 | 47 |
| Components: | | |
| $CF_3$—$CFCl_2$ (end product) | 0.3% | 0.7% |
| $CF_3$—$CCl_3$ (reactant) | 39.3% | 82.2% |
| $CF_3$—$CH_2Cl$ (fluorinating agent) | 53.9% | 14.1% |
| $CF_2$=$CHCl$ (by-product) | 6.1% | 2.2% |
| $CF_3$—$CHCl_2$ (by-product) | 0.4% | 0.7% |
| Conversion based on R113a: | <1.0% | 0.5% |

Comparison Example 2 documents that aluminum fluoride catalysts cannot be used as the transfluorination catalyst.

We claim:

1. A process for the preparation of a partly fluorinated ethane of the formula $$CF_3-CFH_xCl_{2-x}$$

in which x=0, 1 or 2, which comprises reacting, as the reactant, $$CF_3-CH_xCl_{3-x}$$

and, as the fluorinating agent $CF_2ClChCl_2$, $CF_2Cl$—$CH_2Cl$, $CF_3$—$CH_2Cl$ or $CF_3CH_3$, with one another in gaseous form in the presence of a chromium catalyst at temperatures of 150° to 600° C., the reactant and the fluorinating agent having the same chemical structural formula being excluded, the molar ratio of said reactant to said fluorinating agent being 2.2:1 to 4.4:1.

* * * * *